United States Patent
Kaphan et al.

(10) Patent No.: US 11,571,684 B2
(45) Date of Patent: Feb. 7, 2023

(54) LITHIUM ION BATTERY CATHODE AND ANODE MATERIALS AS TUNABLE AND DYNAMICALLY RESPONSIVE SUPPORT MATERIALS FOR SINGLE SITE HETEROGENEOUS CATALYSIS

(71) Applicant: UCHICAGO ARGONNE, LLC, Chicago, IL (US)

(72) Inventors: David Kaphan, Oak Park, IL (US); Massimiliano Delferro, Chicago, IL (US); Alon Chapovetsky, Chicago, IL (US); Cynthia Jeanne Jenks, Elmhurst, IL (US); Christopher S. Johnson, Naperville, IL (US)

(73) Assignee: UChicago Argonne, LLC, Chicago, IL (US)

( * ) Notice: Subject to any disclaimer, the term of this patent is extended or adjusted under 35 U.S.C. 154(b) by 34 days.

(21) Appl. No.: 17/077,630

(22) Filed: Oct. 22, 2020

(65) Prior Publication Data

US 2022/0126277 A1 Apr. 28, 2022

(51) Int. Cl.
  *B01J 23/889* (2006.01)
  *C01G 53/00* (2006.01)
  *B01J 37/02* (2006.01)

(52) U.S. Cl.
  CPC ....... *B01J 23/8892* (2013.01); *B01J 37/0209* (2013.01); *C01G 53/54* (2013.01); *C01P 2002/54* (2013.01)

(58) Field of Classification Search
  CPC .. B01J 23/8892; B01J 37/0209; B01J 23/005; C01G 53/54; C01P 2002/54

USPC .................................................. 502/324, 524
  See application file for complete search history.

(56) References Cited

U.S. PATENT DOCUMENTS

| | | | | |
|---|---|---|---|---|
| 4,567,031 A * | 1/1986 | Riley | ............ | C01G 23/005 423/598 |
| 5,160,712 A * | 11/1992 | Thackeray | ............ | C01G 53/42 429/231.3 |
| 5,609,975 A * | 3/1997 | Hasegawa | ............ | H01M 4/525 427/126.3 |
| 5,789,112 A * | 8/1998 | Ellgen | ............ | H01M 4/525 429/223 |
| 5,900,385 A * | 5/1999 | Dahn | ............ | H01M 4/131 502/313 |
| 6,168,888 B1 * | 1/2001 | Iwata | ............ | H01M 4/505 429/231.95 |
| 7,556,655 B2 * | 7/2009 | Dahn | ............ | C01G 53/006 429/223 |
| 2003/0175191 A1 * | 9/2003 | Hedouin | ............ | B01J 23/34 423/239.1 |
| 2018/0342761 A1 * | 11/2018 | Eaglesham | ............ | H01M 50/126 |

(Continued)

OTHER PUBLICATIONS

Atienza, et al., "Reversible Carbon-Carbon Bond Formation Induced by Oxidation and Reduction at a Redox-Active Cobalt Complex," Inorganic Chemistry 52(9), pp. 5403-5417 (2013).

(Continued)

*Primary Examiner* — Patricia L. Hailey
(74) *Attorney, Agent, or Firm* — Foley & Lardner LLP

(57) ABSTRACT

A method of turning a catalytic material by altering the charge state of a catalyst support. The catalyst support is intercalated with a metal ion, altering the charge state to alter and/or augment the catalytic activity of the catalyst material.

14 Claims, 10 Drawing Sheets

(56) References Cited

U.S. PATENT DOCUMENTS

2021/0113982 A1* 4/2021 Chen .................. C01G 1/02

OTHER PUBLICATIONS

Bailey, et al., "Bimolecular Coupling as a Vector for Decomposition of Fast-Initiating Olefin Metathesis Catalysts," Journal of the American Chemical Society 140(22), pp. 6931-6944 (2018).

Bouwkamp, et al., "Iron-Catalyzed [2pi+ 2pi] Cycloaddition of a,w-Dienes: The Importance of Redox-Active Supporting Ligands," Journal of the American Chemical Society 128(41), pp. 13340-13341 (2006).

Bruix, et al., "A New Type of Strong Metal-Support Interaction and the Production of H2 through the Transformation of Water on Pt/CeO2(111) and Pt/CeOx/TiO2(110) Catalysts," Journal of the American Chemical Society 134(21), pp. 8968-8974 (2012).

Camacho-Bunquin, et al., "Atomically Precise Strategy to a PtZn Alloy Nanocluster Catalyst for the Deep Dehydrogenation of n-Butane to 1,3-Butadiene," ACS Catalysis 8(11), pp. 10058-10063 (2018).

Celik, et al., "Upcycling Single-Use Polyethylene into High-Quality Liquid Products," ACS Central Science 5(11), pp. 1795-1803 (2019).

Chan, et al., "Well-Defined Silica-Supported Tungsten(IV)-Oxo Complex: Olefin Metathesis Activity, Initiation, and Role of Bronsted Acid Sites," Journal of the American Chemical Society 141(45), pp. 18286-18292 (2019).

Chapovetsky, et al., "Activation of Low-Valent, Multiply M-M Bonded Group VI Dimers toward Catalytic Olefin Metathesis via Surface Organometallic Chemistry," Organometallics 39(7), pp. 1035-1045 (2020).

Chapovetsky, et al., "Electronically Modified Cobalt Aminopyridine Complexes Reveal an Orthogonal Axis for Catalytic Optimization for CO2 Reduction," Inorganic Chemistry 59(18), pp. 13709-13718 (2020).

Chen, et al., "[(=SiO)TaVCl2Me2]: A Well-Defined Silica-Supported Tantalum(V) Surface Complex as Catalyst Precursor for the Selective Cocatalyst-Free Trimerization of Ethylene," Angewandte Chemie 124(47), pp. 12056-12059 (2012).

Chen, et al., "A Novel Redox Precipitation to Synthesize Au-Doped a-MnO2 with High Dispersion toward Low-Temperature Oxidation of Formaldehyde," Environmental Science & Technology 52(8), pp. 4728-4737 (2018).

Chen, et al., "Alkane Metathesis with the Tantalum Methylidene [(=SiO)Ta(-CH2)Me2]/[(=SiO)2Ta(-CH2)Me] Generated from Well-Defined Surface Organometallic Complex [(=SiO)TaVMe4]," Journal of the American Chemical Society 137(2), pp. 588-591 (2015).

Chen, et al., "The use of a well-defined surface organometallic complex as a probe molecule: [(=SiO)TaVCl2Me2] shows different isolated silanol sites on the silica surface," Chemical Communications 50(79), pp. 11721-11723 (2015).

Conley, et al., "A Well-Defined Silica-Supported Tungsten Oxo Alkylidene Is a Highly Active Alkene Metathesis Catalyst," Journal of the American Chemical Society 135(51), pp. 19068-19070 (2013).

Conley, et al., "Bulky Aryloxide Ligand Stabilizes a Heterogeneous Metathesis Catalyst," Angewante Chemie 53(51), pp. 14221-14224 (2014).

Coperet, et al., "Surface Organometallic and Coordination Chemistry toward Single-Site Heterogeneous Catalysts: Strategies, Methods, Structures, and Activities," Chemical Reviews 116(2), pp. 323-421 (2016).

Coperet, et al., "Surface Organometallic Chemistry: Paving the Way Beyond Well-Defined Supported Organometallics and Single-Site Catalysis," Catalysis Letters 147, pp. 2247-2259 (2017).

Darmon, et al., "Oxidative Addition of Carbon-Carbon Bonds with a Redox-Active Bis(imino)pyridine Iron Complex," Journal of the American Chemical Society 134(41), pp. 17125-17137 (2012).

Dufour, et al., "Surface organometallic chemistry: reaction of tris(allyl)rhodium with surfaces of silica, alumina, titania, and magnesia. [Erratum to document cited in CA116(23):235831z]," Hournal of the AMerican Chemical Society 114(11), pp. 4248-4257 (1992).

Fan, et al., "Single-site nickel-grafted anatase TiO2 for hydrogen production: Toward understanding the nature of visible-light photocatalysis," Journal of Catalysis 320, pp. 147-159 (2014).

Fujdala & Tilley, "Design and synthesis of heterogeneous catalysts: the thermolytic molecular precursor approach," Journal of Catalysis 216(1-2), pp. 265-275 (2003).

Grasser, et al., "Structures of paramagnetic Viv amido complexes grafted onto metal oxide surfaces: Model systems for heterogeneous vanadium catalysts," Physical Chemistry Chemical Physics 5(9), pp. 1906-1911 (2003).

Gunasooriya, et al., "Ethylene Hydrogenation over Pt/TiO2: A Charge-Sensitive Reaction," ACS Catalysis 7(3), pp. 1966-1970 (2017).

Guzman, et al., "Formation of Gold Clusters on TiO2 from Adsorbed Au(CH3)2(C5H7O2): Characterization by X-ray Absorption Spectroscopy," Catalysis Letters 95, pp. 77-86 (2004).

Hamieh, et al., "Well-Defined Surface Species [(=Si—O—)W(-O)Me3] Prepared by Direct Methylation of [(=Si—O—)W(-O)Cl3], a Catalyst for Cycloalkane Metathesis and Transformation of Ethylene to Propylene," ACS Catalysis 5(4), pp. 2164-2171 (2015).

Huang, et al., "A Long-Lived Mononuclear Cyclopentadienyl Ruthenium Complex Grafted onto Anatase TiO2 for Efficient CO2 Photoreduction," Angewandte Chemie 55(29), pp. 8314-8318 (2016).

Ioannides & Verykios, "Charge Transfer in Metal Catalysts Supported on Doped TiO2: A Theoretical Approach Based on Metal-Semiconductor Contact Theory," Journal of Catalysis 161 (2), pp. 560-569 (1996).

Iwasawa & Sato, "Preparations of TiO2-Attached Rn Catalysts and their Catalysis," 14(4), pp. 507-510 (1985).

Jeantelot, et al., "TiO2-supported Pt single atoms by surface organometallic chemistry for photocatalytic hydrogen evolution," Physical Chemistry Chemical Physics 21(44), pp. 24429-24440 (2019).

Kaphan, et al., "Mechanistic Aspects of a Surface Organovanadium(III) Catalyst for Hydrocarbon Hydrogenation and Dehydrogenation," ACS Catalysis 9(12), pp. 11055-11066 (2019).

Klet, et al., "Evidence for Redox Mechanisms in Organometallic Chemisorption and Reactivity on Sulfated Metal Oxides," Journal of the American Chemical Society 140(20), pp. 6308-6316 (2018).

Lam, et al., "Zr(IV) surface sites determine CH3OH formation rate on Cu/ZrOZ/SiO2—CO2 hydrogenation catalysts," Chinese Journal of Catalysis 40(11), pp. 1741-1748 (2019).

Langeslay, et al., "Nuclearity effects in supported, single-site Fe(ii) hydrogenation pre-catalysts," Dalton Transactions 47(32), pp. 10842-10846 (2018).

Lebedev, et al., "Atomically Dispersed Iridium on Indium Tin Oxide Efficiently Catalyzes Water Oxidation," ACS Central Science 6(7), pp. 1189-1198 (2020).

Lebedev, et al., "The Key RuV=O Intermediate of Site-Isolated Mononuclear Water Oxidation Catalyst Detected by in Situ X-ray Absorption Spectroscopy," Journal of the American Chemical Society 140(1), pp. 451-458 (2018).

Lu, et al., "Electrochemical tuning of layered lithium transition metal oxides for improvement of oxygen evolution reaction," Nature Communications 5, 4345, 7 pages (2014).

Samantaray, et al., "The Comparison between Single Atom Catalysis and Surface Organometallic Catalysis," Chemical Reviews 120(2), pp. 734-813 (2020).

Samantaray, et al., "WMe6 Tamed by Silica: =Si—O—WMe5 as an Efficient, Well-Defined Species for Alkane Metathesis, Leading to the Observation of a Supported W-Methyl/Methylidyne Species," Journal of the American Chemical Society 136(3), pp. 1054-1061 (2014).

Schwab & Koller, et al., "Combined action of metal and semiconductor catalysts," Journal of the American Chemical Society 90(12), pp. 3078-3080 (1968).

Sheehan, et al., "A molecular catalyst for water oxidation that binds to metal oxide surfaces," Nature Communications 6, 6469, 9 pages (2015).

Sohn, et al., "Isolated, well-defined organovanadium(iii) on silica: single-site catalyst for hydrogenation of alkenes and alkynes," Chemical Communications 53, pp. 7325-7328 (2017).

(56) References Cited

OTHER PUBLICATIONS

Syed, et al., "Electrophilic Organoiridium(III) Pincer Complexes on Sulfated Zirconia for Hydrocarbon Activation and Functionalization," Journal of the American Chemical Society 141(15), pp. 6325-6337 (2019).
Tondreau, et al., "Synthesis and Electronic Structure of Cationic, Neutral, and Anionic Bis(imino)pyridine Iron Alkyl Complexes: Evaluation of Redox Activity in Single-Component Ethylene Polymerization Catalysts," Journal of the American Chemical Society 132(42), pp. 15046-15059 (2010).
Wang, et al., "Direct and continuous strain control of catalysts with tunable battery electrode materials," Science 354(6315), pp. 1031-1036 (2016).
Wang, et al., "Electrochemical tuning or vertically aligned MoS2 nanofilms and its application in improving hydrogen evolution reaction," Proceedings of the National Academy of Sciences 110(49), pp. 19701-19706 (2013).
Witzke, et al., "Nontraditional Catalyst Supports in Surface Organometallic Chemistry," ACS Catalysis 10(ASAP), pp. 11822-11840 (2020).
Xia, et al., "Enhanced Performance and Conversion Pathway for Catalytic Ozonation of Methyl Mercaptan on Single-Atom Ag Deposited Three-Dimensional Ordered Mesoporous MnO2," Environmental Science & Technology 52(22), pp. 13399-13409 (2018).
Zhang, et al., "Catalytic chemoselective functionalization of methane in a metal-organic framework," Nature Catalysis 1, pp. 356-362 (2018).

\* cited by examiner

US 11,571,684 B2

LITHIUM ION BATTERY CATHODE AND ANODE MATERIALS AS TUNABLE AND DYNAMICALLY RESPONSIVE SUPPORT MATERIALS FOR SINGLE SITE HETEROGENEOUS CATALYSIS

STATEMENT OF GOVERNMENT INTEREST

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present disclosure relates to catalysts, more specifically to tunable support materials for single site catalysis.

BACKGROUND

Catalysts play an important role in a wide range of research, commercial, and industrial processes. Heterogeneous catalysis relies upon a catalytic material on a support. However, broadly applicable strategies for continuous control of activity and selectivity in heterogeneous catalysis remains a desirable goal in the field. The heterogenization of organometallic catalysts on metal oxide supports through surface organometallic chemistry ("SOMC") is a powerful strategy for developing heterogeneous, single-site, and homogeneous-in-function catalysts. In these systems, the support plays a crucial role in stabilizing and site-isolating reactive intermediates on the surface while imparting advantageous physical properties including recyclability and lower catalyst separation costs. The performance of the supported system is often dictated by the catalytic activity of the homogeneous fragment, often enhanced by site isolation on the surface. Traditional heterogeneous catalysis focused on the catalytic material while considering the support material in terms of stabilization and catalyst loading parameters. In current heterogeneous catalysis, the role of the support is as a high surface area dispersant for the catalytically active species.

Thus, there remains a need for a process which utilizes the tuning of support structures for alteration and optimization of catalytic material performance in heterogeneous catalysis.

SUMMARY

One embodiment relates to a method of tuning a catalyst comprising providing a catalyst support precursor having a catalytic metal bound thereto; intercalating the catalyst support with a metal ion; and altering the catalytic support precursor by addition of a charge.

Another embodiment relates to a method of forming a catalyst comprising providing a catalytic support precursor comprising a ternary oxide; binding a catalytic metal to the catalytic support precursor, where the catalytic metal has a sub-monolayer on the catalytic support precursor, forming an untuned catalyst material; and altering a charge state of the untuned catalyst material forming a tuned catalyst material.

Yet another embodiment relates to a catalyst comprising $Ni_yLi_xMn_2O_4$, where y is 0.40 to 0.6 and wherein the ratio of Li to Mn is 0.48 to 1.12.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE FIGURES

The foregoing and other features of the present disclosure will become more fully apparent from the following description and appended claims, taken in conjunction with the accompanying drawings. Understanding that these drawings depict only several implementations in accordance with the disclosure and are, therefore, not to be considered limiting of its scope, the disclosure will be described with additional specificity and detail through use of the accompanying drawings.

FIG. 11A shows reaction progress for the hydrogenation of cyclohexene with Ni@Li$_{1.94}$Mn$_2$O$_4$. FIG. 11B shows reaction progress for the hydrogenation of cyclohexene with Ni@Li$_{2.06}$Mn$_2$O$_4$. FIG. 11C shows reaction progress for the hydrogenation of cyclohexene with Ni@Li$_{2.10}$Mn$_2$O$_4$. FIG. 11D shows reaction progress for the hydrogenation of cyclohexene with Ni@Li$_{2.16}$Mn$_2$O$_4$. FIG. 11E shows reaction progress for the hydrogenation of cyclohexene with Ni@Li$_{2.22}$Mn$_2$O$_4$.

Figure 1A:
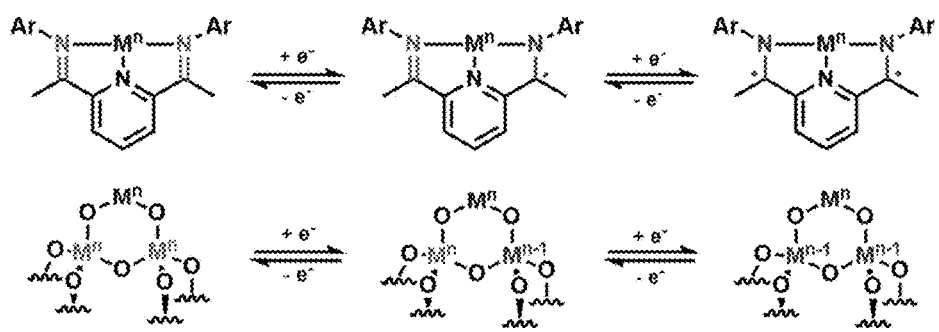
FIG. 1A shows an analogy between redox non-innocent molecular ligands and comparable redox non-innocence of a solid catalyst support.
Figure 1B:
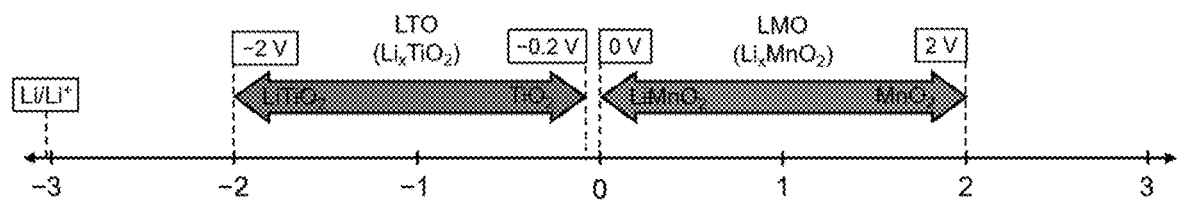
FIG. 1B shows surface potentials achievable by redox tuning of two battery anode/cathode materials, lithium titanate, and lithium manganese oxide.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

While materials for catalysis often focus on the catalytic material directly, the support material can play a vital role in the catalytic system. In one embodiment, rather than treating the supports as a physical structure for providing a high surface area for catalyst loading, the support is viewed as an integral part of the overall catalytic system, operating as a chemically dynamic ligand. The chemically dynamic ligand supports can be tuned to provide a desired electronic structure to alter or augment the catalytic activity of the catalyst.

In one embodiment, the chemically dynamic ligand supports are organic support ligands. Organic support ligands play an intimate role in determining the reactivity of the metal that they stabilize. Their electronic characteristics, as characterized by their σ- and π-donor and acceptor properties as well as other parameters, have been shown to serve as useful handles for manipulating catalyst activity and selectivity. For example, recent work by Marinescu and coworkers showed that electronic modification of an organic ligand can serve as an orthogonal axis for catalyst optimization. Beyond control over the electronics of the metal center, the redox properties of conjugated organic ligands also allow them to play an active role in the reversible storage of electrons in catalytic processes. These so-called "redox non-innocent ligands" facilitate key chemical steps by storing and transferring electrons to the catalyst during key steps throughout the catalytic cycle. Chirik and coworkers showed that metal complexes stabilized by redox active diimine pincer ligands enable difficult multi-electron transformations via mechanisms that invoke ligand based oxidative additions.

Electronic metal support interactions ("EMSI"), a heterogeneous analogy to redox non-innocent ligands, are understood as a likely explanation for the observed cooperativity between nanoparticles and support materials in heterogeneous catalysis. While the role of EMSI in heterogeneous catalysis is gaining increasing recognition in the field, there are relatively few examples of leveraging EMSI to actively modulate catalytic reaction outcomes. Further, even for the few examples of SOMC systems that employ EMSI capable supports, the presence of a discrete EMSI interaction has not been conclusively demonstrated and nor has it been utilized to tune catalytic reactivity. It is believed that a redox active inorganic support material can operate similar to a redox non-innocent ancillary ligand, harnessing the ability to finely tune the characteristics of the support, such as Fermi level, band structure, and/or surface potential.

In a general catalytic cycle, the metal/active site undergoes elementary steps that consist of oxidation/reduction. In a traditional catalyst, the metal is both the active site and the species to be oxidized/reduced. It is believed that in the examples provided herein, the metal/active site retains its oxidation state throughout the catalytic cycle, and it is the support that gets oxidized and reduced. The addition of charge to the support enables easier oxidation, thus, accelerating the reaction rate. In one embodiment, supports that may function as a catalyst precursor support are those that may undergo a redox reaction with an alkaline earth metal. Preferably, the catalyst precursor support is a material that is able to be intercalated by an alkali earth metal, such as lithium or sodium. More generally some support materials, such as oxides for use in batteries, have a driving force for reaction that is associated with the composition content of lithium. Catalyst support precursors may be various 1D to 3D materials, such as ternary metal oxides including spinel and layered forms. Therefore, while the Mn- and Ti-spinel oxide show effective catalytic affect, other materials like the layered class of family of Li$_y$MO$_{2+\delta}$, where M is a collection of transition metals (e.g., Ni, Co, Mn, so called 'NMC' or vanadium), y is between 0≤y<1, and δ≈2, will be tunable by addition of charge via change in lithium content. This tunability allows for changing the products and distributions of catalysis using the same catalytic metal and catalytic support precursor but different amounts of charge addition (via lithium addition). In addition NCA (LiNi$_{0.8}$Co$_{0.15}$Al$_{0.05}$O$_2$), and LCO (LiCoO$_2$) layered compounds can be employed as well. The above compounds are 2D layered gallery materials, 3D LiMn$_2$O$_4$, and by extension LiNi$_{0.5}$Mn$_{1.5}$O$_4$ (i.e., 5V spinel). Certainly the driving force of 5V spinel with nominal voltage 4.7V.

A catalyst support precursor is prepared. The catalyst support precursor may be known catalyst support materials that provide a high surface area. In some embodiments, the catalyst support precursor is an electrode material having a range of charge state that are continuously tunable, such as lithium intercalation materials. The catalyst support precursor may be formed in accordance with known techniques. The catalyst support precursor than undergoes a change in the charge state. The changing of the charge state of the catalyst support precursor. In one embodiment, the catalyst support precursor is a lithium oxide, and the changing in the charge state is via lithiation.

In one embodiment, supports are modified by adding a charge. Some examples herein utilize a process for adding Li and electron equivalents, via agents (n-Butyl Lithium and Lithium Napthalide) into the support. However, such are non-limiting examples and further agents may be selected to modify the support to add a charge, such as other alkyl lithium reagents. Further embodiments may charge the support electrochemically, the same way one would charge a battery. Such embodiments would comprise solid Li and electrolyte solution.

In some embodiments, cathode and anode materials, such as lithium manganese oxide and lithium titanate, are attractive candidates for redox active supports due to the range of accessible charge states continuously tunable as a function of the degree of lithium intercalation, resulting with tunable surface potential while maintaining a similar local active site geometry. Certain embodiments relate to manganese oxide grafted nickel catalysts.

A catalyst is then added to the catalyst support precursor, for example by grafting or other known mechanisms. The catalyst metal that is bounded or engaged with the catalyst support precursor may be selected from the group consisting of any transition metal, lanthanide/actinide, and main group element that can bind substrates (e.g., Ni for LiMnO$_2$ or Fe for LiTiO$_2$ catalyst support precursors, respectively). In addition to grafting, ligand abstraction, condensation, and protonolysis can be used.

Regardless of the technique used, the catalytic metal and supports must be compatible. For example, for protonolysis to occur the support must have —OH groups on the surface and the metal precursor must have basic ligands that can be protonated, for example as used in the TiO$_2$ examples herein. In the Ni(COD)$_2$ embodiment in the examples below, the Ni reduction potential is compatible with the support oxidation potential so that the support oxidatively adds to it.

The catalytic reaction using the tuned catalyst materials results in a reaction occurring at the catalytic metal sites on the catalyst support. Thus, the catalytic metal loading should be such that the support remains exposed and the catalytic metal is less than a monolayer. In some embodiments, the catalytic metal is atomically dispersed, in other embodiments the catalytic metal is dispersed with an atom per 1-10 nm$^2$. In the results shown below, the Ni content remains roughly the same, with the variation in overall wt % due to the fact that Li is added to the material. It is preferred to retain single sites on the surface as opposed to a monolayer. Subsequently for embodiments such as those illustrated below, the catalytic metal loading is below 6-10 atoms/nm$^2$. It should be appreciated that this single site structure translates to a different loading depending on the surface area of the support.

The untuned catalyst material comprising the catalyst and catalyst support precursor, is then tuned to adjust the properties as desired. In one embodiment, the adjustment is by intercalation of a metal ion into the catalyst support precursor structure, with exposure of the untuned catalyst support precursor to a metal precursor to replace some of the support with lithium.

For embodiments utilizing lithiation, the lithium reagent must have a more reducing potential compared to the support being reduced. Embodiments may include alkyl lithium reagents (n-Butyllithium) and aryl lithium reagents (lithium napthalide). It is believed that for an alkyl lithium reagent to be compatible it must be able to undergo a β-hydride elimination, indicating that n-Butyllithium, sec-butyllithium, and iso-butyl lithium reagents are all compatible. Likewise, for an aryl lithium reagents Li Napthalide and Anthracenide may be utilized work.

In one embodiment, the catalyst material comprises Ni$_y$Li$_x$Mn$_2$O$_4$ where y is 0.40 to 0.6 and wherein the ratio of Li to Mn is 0.48 to 1.12, for example where x is 0.96 to 2.23.

As described further herein and supported by the experimental results described below, the catalysts show that their activity is directly proportional to the charge state of the support material. Further, generality of the phenomenon observed with specific embodiments is demonstrated by extension to a system where the reactivity of an organotantalum complex on TiO$_2$ is engineered by exhaustive lithiation of the complex and support material.

EXPERIMENTS

Figure 2A:
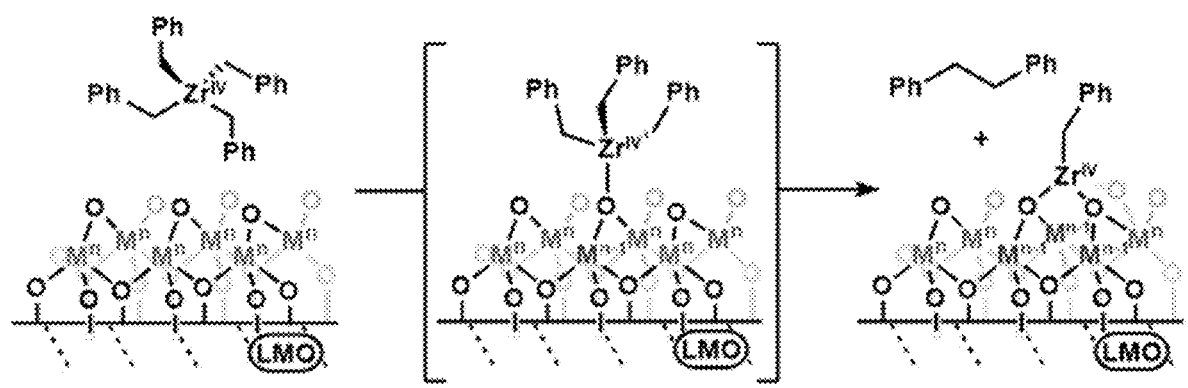
FIG. 2A illustrates one embodiment of a redox non-innocent surface modification strategy, and $Zr^{iv}$ can be any element that can bind with the substrates and Ph, which can be any organic or inorganic ligand that is bound to the metal ranging from halides (Cl, Br, etc.) to organic groups (C, N, O, and S based, etc.).
Figure 2B:
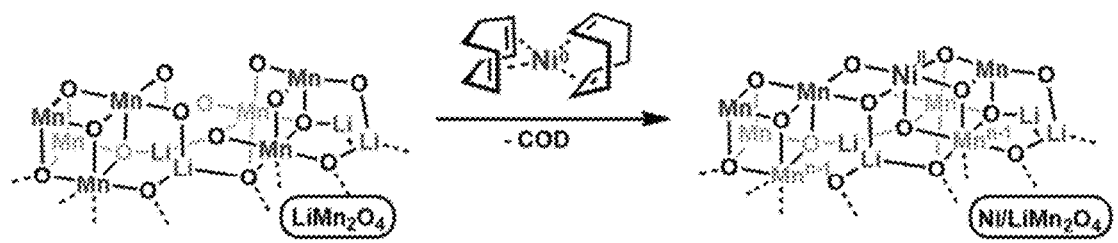
FIG. 2B shows an example of oxidative grafting of $Ni(COD)_2$ onto $LiMn_2O_4$.
Figure 2C:
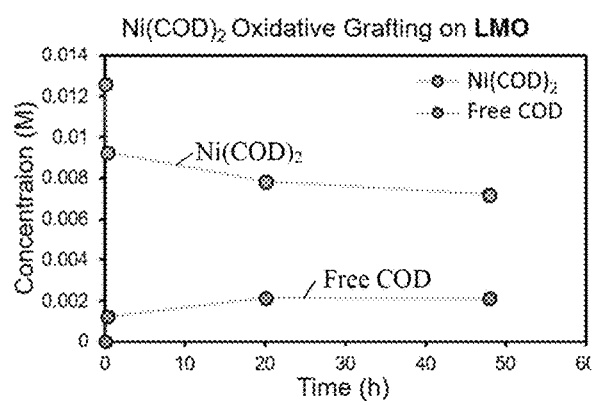
FIGS. 2C-2D show graphs of the concentration of $Ni(COD)_2$ and free COD over time for $LiMn_2O_4$ substrate (FIG. 2C) and for a silica substrate (FIG. 2D).

Synthesis and characterization. Li$_{0.96}$Mn$_2$O$_4$ was prepared according to literature procedures. Addition of a yellow solution of bis(cyclooctadiene)nickel(0) ("Ni(cod)$_2$") to a suspension of Li$_{0.96}$Mn$_2$O$_4$ (pretreated under vacuum at 200° C., surface area=10 m$^2$/g) and mechanical agitation over the course of one hour resulted in the deposition of the nickel precursor onto the metal oxide (Ni@Li$_{0.96}$Mn$_2$O$_4$, 0.45 wt % Ni) and a pale yellow supernatant solution. Tracking the deposition reaction by $^1$H nuclear magnetic resonance ("NMR") spectroscopy using 1,3,5-tri-$^t$Bu-benzene as an internal standard revealed a decrease in the amount of nickel precursor in solution and the appearance of free cyclooctadiene (FIG. 2B, left). Addition of excess bipyridine or triphenylphosphine ligands to a (washed and dried) suspension of Ni@Li$_{0.96}$Mn$_2$O$_4$ in C$_6$D$_6$ and subsequent tracking did not result in the appearance of free cyclooctadiene ligand in solution. Thermogravimetric analysis ("TGA") of Ni@Li$_{0.96}$Mn$_2$O$_4$ similarly did not produce evidence of the presence of cyclooctadiene in the material. Results from the NMR and TGA experiments suggest that upon grafting both cyclooctadiene ligands dissociate from the nickel precursor.

Lithiation of Ni@Li$_{0.96}$Mn$_2$O$_4$ was performed using n-Butyllithium in pentane. In a typical experiment, n-Butyllithium solution (2.5M) was added to a suspension of Ni@Li$_{0.96}$Mn$_2$O$_4$ in pentane at −36° C. and the reaction mixture was mechanically agitated over the course of 20 hours. Addition of different amounts of n-Butyllithium gave rise to a series of materials with varying extents of lithiation Ni@Li$_x$Mn$_2$O$_4$ (x=0.96 to 2.24, see Table 1 for more details).

TABLE 1

ICP data for the Ni@Li$_x$Mn$_2$O$_4$ materials.

| Ni wt % | Li/Mn ratio | Chemical Formula |
|---|---|---|
| 0.52 | 0.48 | Li$_{0.96}$Mn$_2$O$_4$ |
| 0.51 | 0.63 | Li$_{1.26}$Mn$_2$O$_4$ |
| 0.43 | 0.77 | Li$_{1.54}$Mn$_2$O$_4$ |
| 0.50 | 0.82 | Li$_{1.64}$Mn$_2$O$_4$ |
| 0.49 | 0.90 | Li$_{1.80}$Mn$_2$O$_4$ |
| 0.48 | 0.97 | Li$_{1.94}$Mn$_2$O$_4$ |
| 0.48 | 1.03 | Li$_{2.06}$Mn$_2$O$_4$ |
| 0.48 | 1.05 | Li$_{2.10}$Mn$_2$O$_4$ |
| 0.45 | 1.08 | Li$_{2.16}$Mn$_2$O$_4$ |
| 0.45 | 1.12 | Li$_{2.24}$Mn$_2$O$_4$ |

Table 1. ICP data for the Ni@Li$_x$Mn$_2$O$_4$ materials.

Figure 2D:
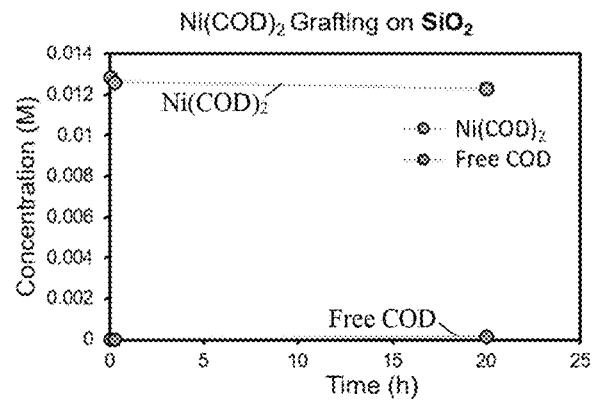

An analogous grafting experiment was performed with partially dehydroxylated silica (Davisil-646, pretreated under vacuum at 700° C., hydroxyl density=1.15 OH nm$^{-2}$) did not result in any nickel grafting on the surface, suggesting that the surface potential of the Li$_{0.96}$Mn$_2$O$_4$ support is crucial for grafting (FIG. 2D).

Figure 3:
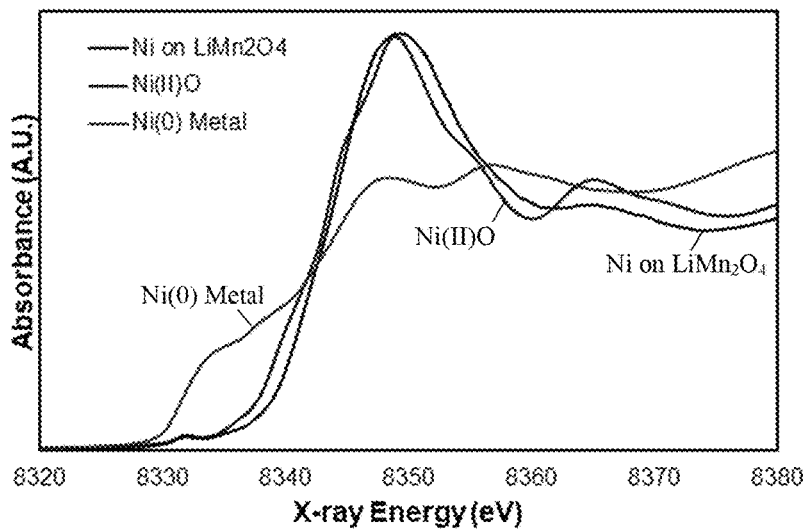
FIG. 3 shows Ni x-ray absorption near edge structure ("XANES") spectra of $Ni@Li_{0.96}Mn_2O_4$, Ni(II)O, and Ni(0) metal. The relative positions of the edges and white lines support a conclusion of a Ni(II) on the surface. The experimental spectrum was most consistent with that of Ni(II), suggesting that upon grafting the nickel atoms were oxidized from Ni(0) to Ni(II). The Mn XANES spectrum for $Ni@Li_{0.96}Mn_2O_4$ was consistent with a material made up of Mn(IV)/Mn(III).

The resultant materials were characterized using X-ray absorption spectroscopy to verify the oxidation states of Ni and Mn and derive insight into the extended structure of the material. The Ni XANES spectrum of Ni@Li$_{0.96}$Mn$_2$O$_4$ (FIG. 3) was compared to a series of nickel standards with varying oxidation states.

Figure 4A:
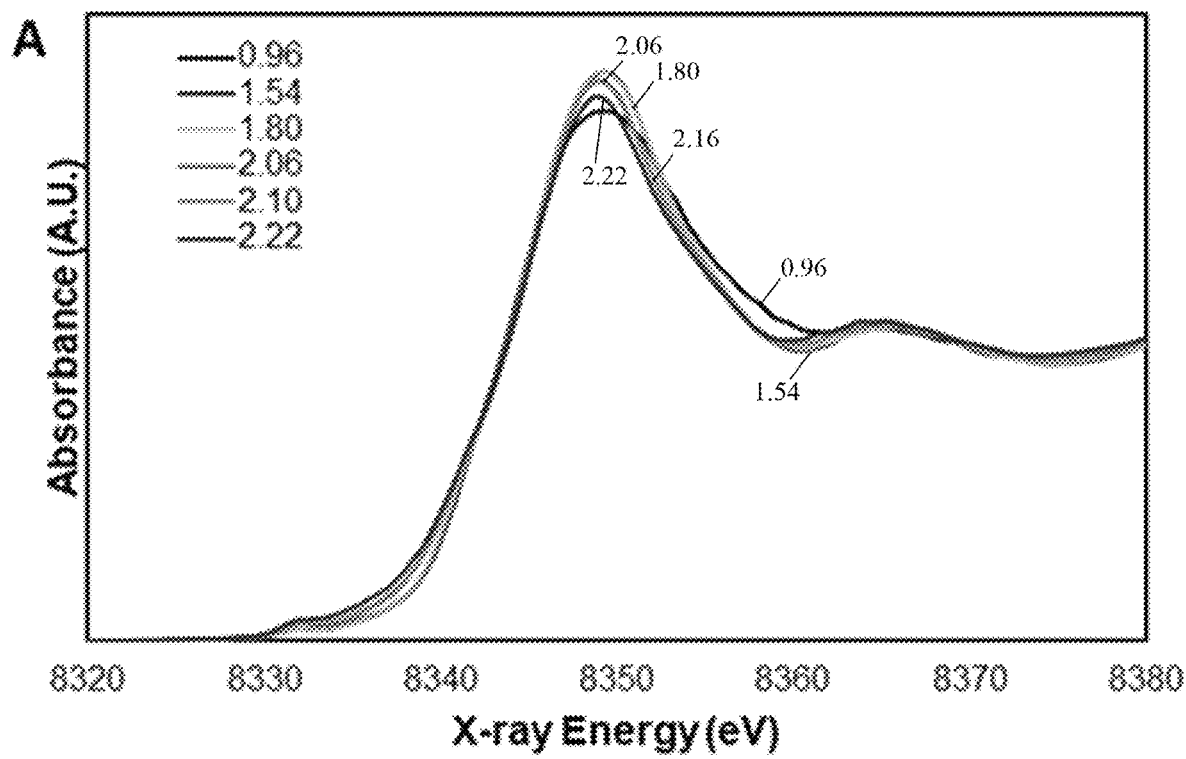
FIGS. 4A-4B show Ni (FIG. 4A) and Mn (FIG. 4B) XANES spectra of a series of materials of the form $Li_xMn_2O_4$ where x is varied between 0.96 and 2.22. The relative positions of the edges and white lines support the conclusion that upon reduction the Ni(II) retains its oxidations state while the Mn is reduced to Mn(III) from Mn(IV).
Figure 4B:
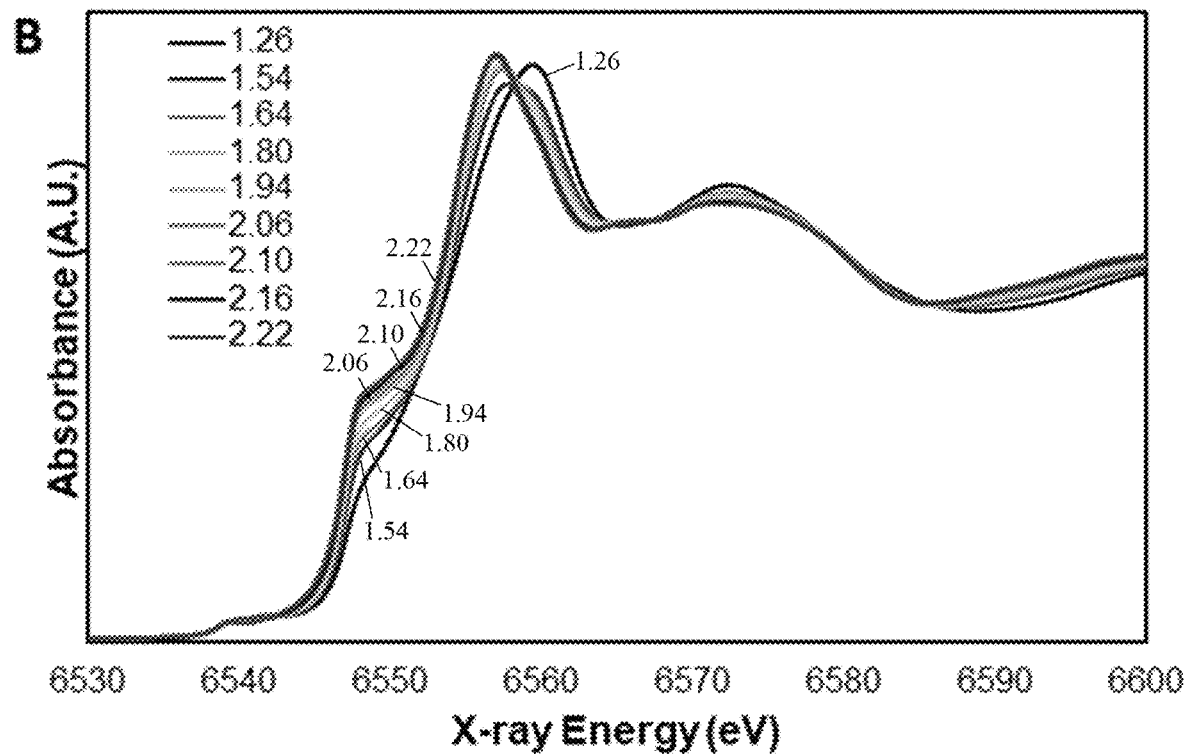
Figure 5:
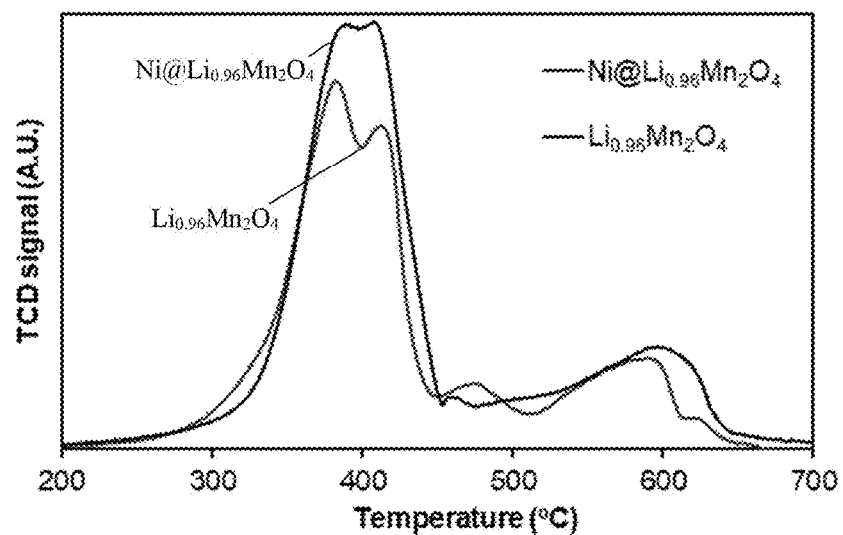
FIG. 5 shows TPR traces for $Ni@Li_{0.96}Mn_2O_4$ and $Li_{0.96}Mn_2O_4$ showing consistent behavior from both materials under similarly reducing conditions. This observation helps rule out the presence of nanoparticles on the surface.

Upon reduction with n-Butyllithium, the oxidation state of the nickel on the surface remained consistent regardless of the amount of reducing equivalents added (FIG. 4A). Upon lithiation, a leftward shift in the white line, along with the appearance of a pre-edge feature at 6545 eV, is suggestive of the gradual reduction of the high valent manganese sites to give a material consisting of purely Mn(III) (FIG. 4B). To further confirm that hypothesis, temperature programmed reduction experiments on Li$_{0.96}$Mn$_2$O$_4$ and Ni@Li$_{0.96}$Mn$_2$O$_4$ show quantitatively identical traces for both materials, consistent with a reduction of the support (FIG. 5).

Figure 6A:
FIG. 6A shows a reaction scheme for the hydrogenation of cyclohexene to make cyclohexane.
Figure 6B:
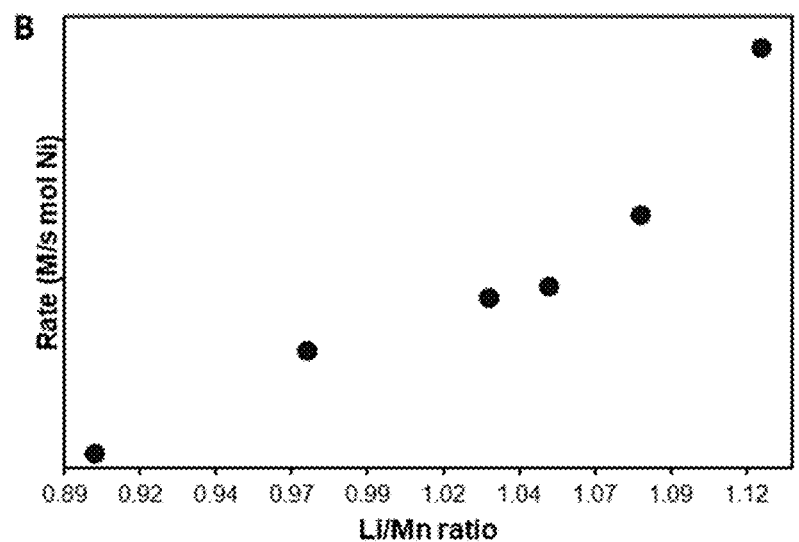
FIG. 6B shows cyclohexene hydrogenation rates (M/s mol Ni) for materials of the form $Ni@Li_xMn_2O_4$ (x=0.96-2.24) plotted as a function of each materials Li/Mn ratio.

Reactivity studies with Ni@Li$_x$Mn$_2$O$_4$ (x=0.96 to 2.24). The catalytic hydrogenation of alkenes was chosen as a model reaction for probing the effect of lithiation on the catalytic activity of the grafted metal. In a typical experiment, H$_2$ gas (~4 atm) was added to a suspension of cyclohexene (olefin substrate, 0.1 M), manganese oxide material (1 mol % Ni), and 1,3,5-tri-$^t$Bu-benzene (internal standard, 1 mM) in C$_6$D$_6$ and the course of the reaction was monitored using $^1$H NMR spectroscopy. Screened materials include the variably reduced Li$_x$Mn$_2$O$_4$ supported nickel materials (Table 1) along with the nickel free partially and fully lithiated metal oxides (Li$_{0.96}$Mn$_2$O$_4$ and Li$_{2.xx}$Mn$_2$O$_4$) as controls. No activity was observed for Li$_{0.96}$Mn$_2$O$_4$ and Li$_{2.x}$Mn$_2$O$_4$ suggesting that catalytic activity hinged on the presence of nickel in the sample. The nickel containing materials exhibited catalytic activity at Li/Mn ratios of 0.9 (x=1.80) and above (FIGS. 10-15). Upon further lithiation beyond x=1.80 the catalytic activity of the material increased as a function of lithium content in the support (FIG. 6). A positive correlation was observed between the rate of hydrogenation and the extent of lithiation in the material.

Figure 7:
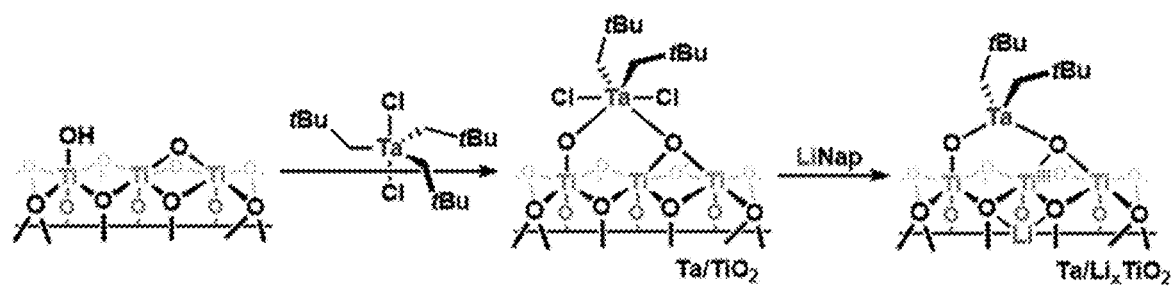
FIG. 7 shows a synthesis of $Ta/TiO_2$ by chemisorption of $TaNp_3Cl_2$ onto $TiO_2$ nanoparticles, followed by global reduction with LiNap to form $Ta/Li_xTiO_2$.
Figure 8:
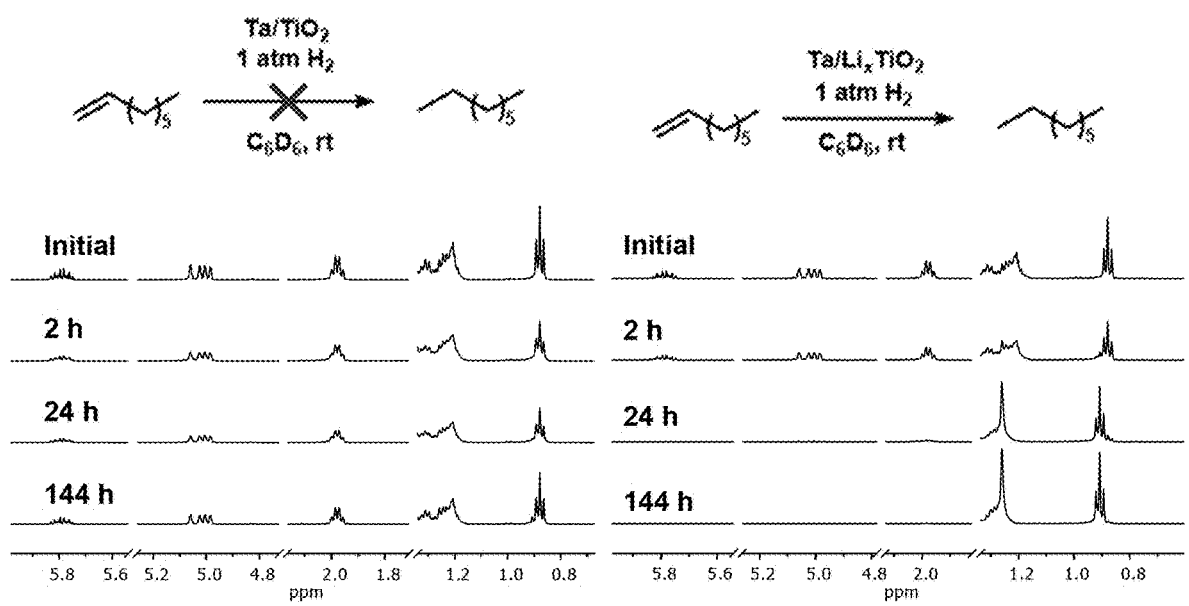
FIG. 8 shows a comparison between the activity of $Ta/TiO_2$ (left) and $Ta/Li_xTiO_2$ (right) towards the catalytic hydrogenation of cyclohexene to make cyclohexane as shown in FIG. 7.
Figure 9:
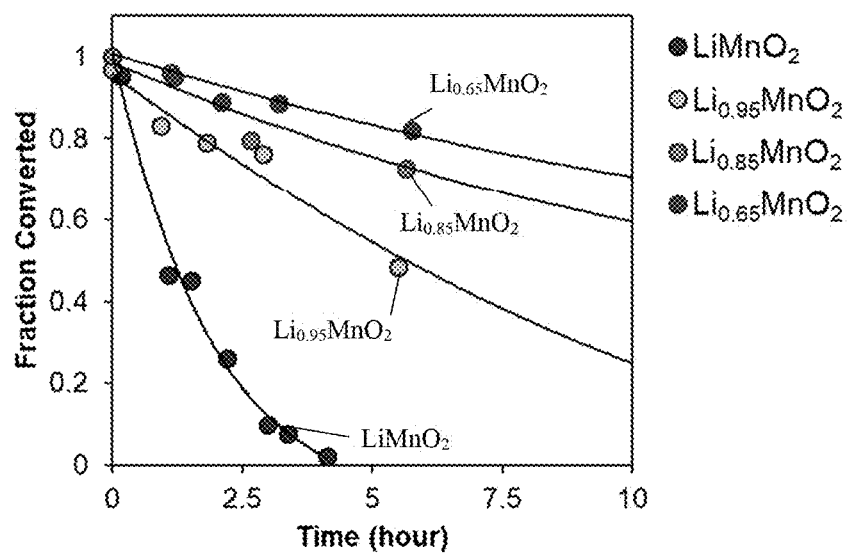
FIG. 9 shows the fraction of cyclohexane conversion over time for $Ni@LiMnO_2$, $Ni@Li_{2.25}MnO_2$, $Ni@Li_{2.07}MnO_2$, and $Ni@Li_{1.72}MnO_2$, depicting the concentration of cyclohexene over time in the presence of $H_2$ and catalyst. The rate of decrease in the concentration of cyclohexene is directly proportional to the rate the catalyst in solution.
Figure 10:
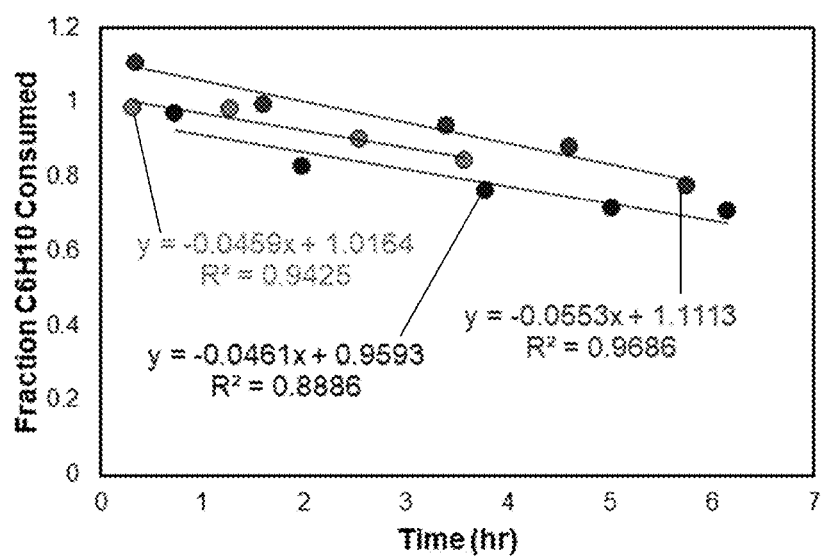
FIG. 10 shows reaction progress for the hydrogenation of cyclohexene with Ni@Li$_{1.8}$Mn$_2$O$_4$.
Figure 11A:
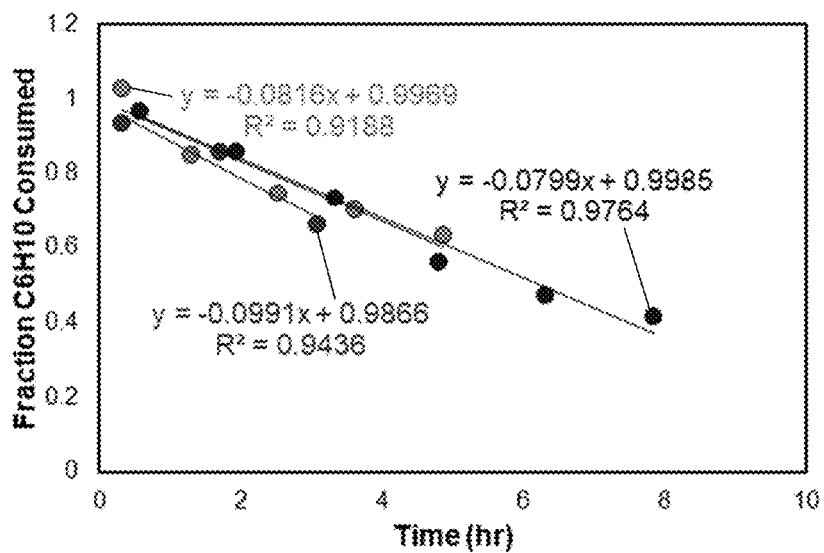
FIGS. 11A-11E depict the concentration of cyclohexene over time in the presence of H$_2$ and catalyst as monitored using $^1$H NMR spectroscopy. The rate of decrease in the concentration of cyclohexene is directly proportional to the rate the catalyst in solution. This rate is shown as a function of catalyst lithiation. The extracted rates are plotted in FIG. 6B vs. the Li/Mn ratio.
Figure 11B:
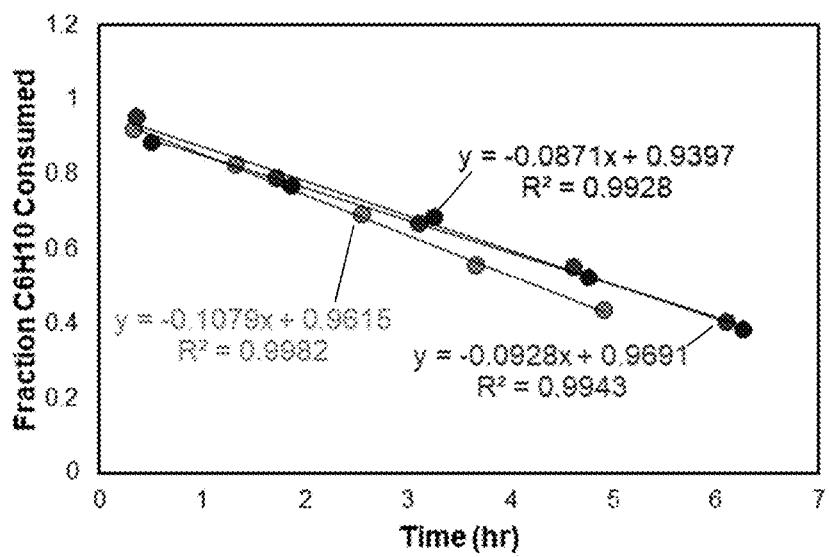
Figure 11C:
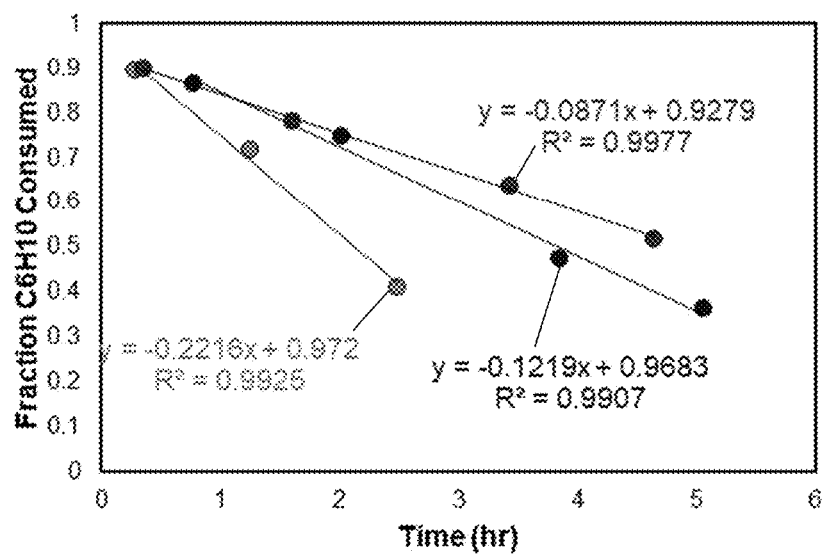
Figure 11D:
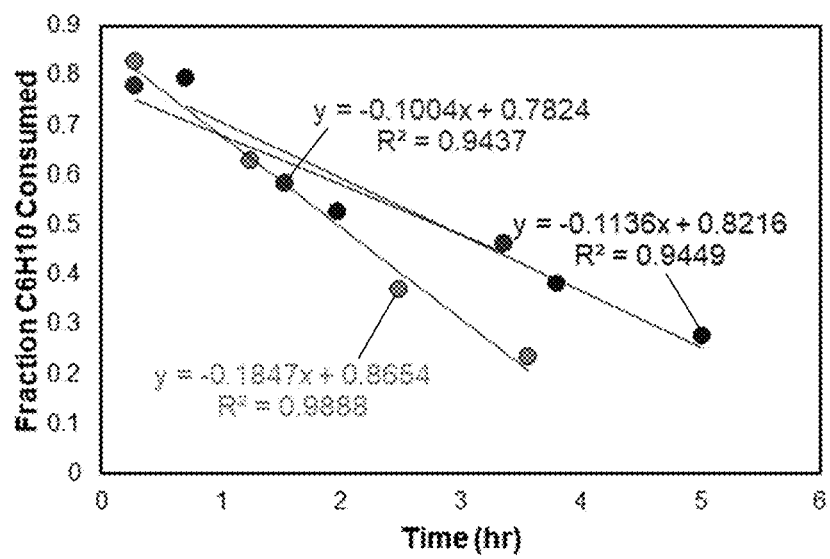
Figure 11E:
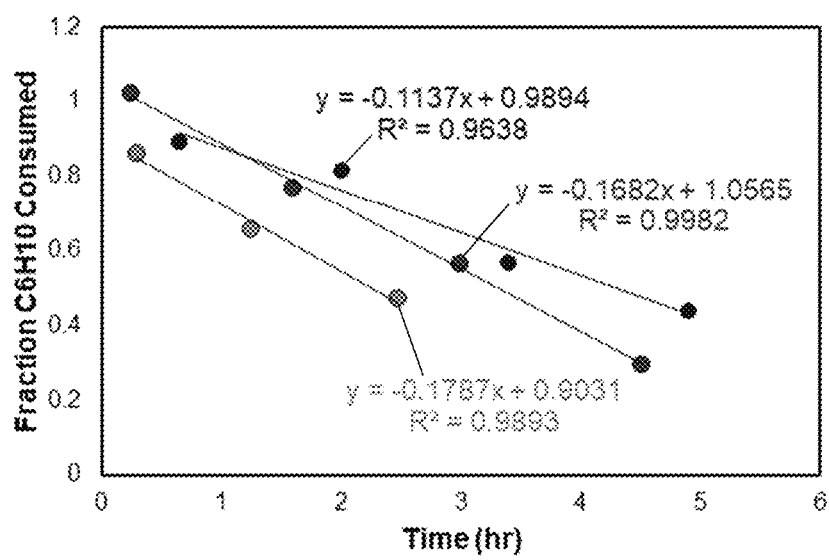
Figure 12A:
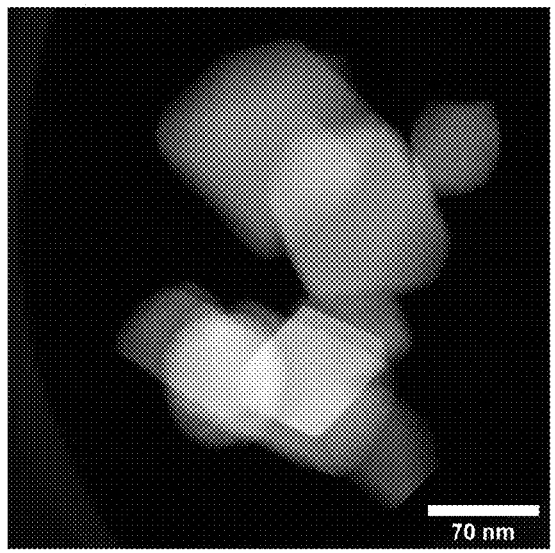
FIG. 12A is a transmission electron microscopy ("TEM") image of Ni@Li$_{0.96}$Mn$_2$O$_4$ showing the morphology of the particles.
Figure 12B:
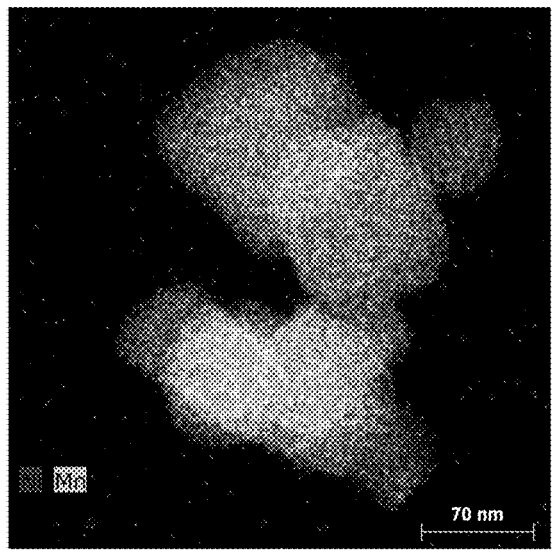
FIG. 12B is elemental mapping of manganese and nickel for Ni@Li$_{0.96}$Mn$_2$O$_4$ using TEM-energy-dispersive x-ray spectroscopy ("EDS"). The Ni data suggests that Ni is dispersed on the surface of the support and is not agglomerated.
Figure 13A:
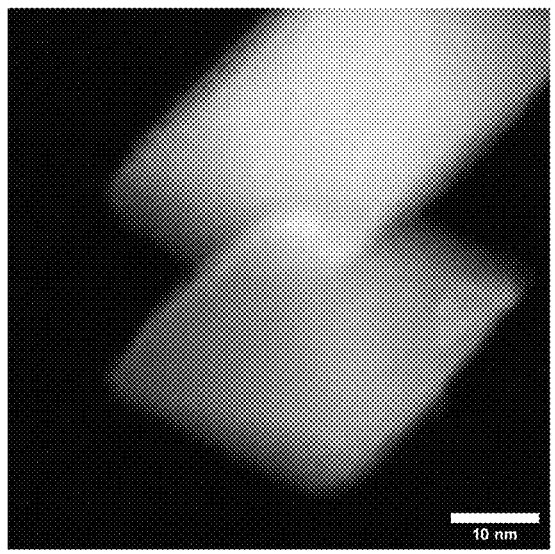
FIG. 13A is a TEM image of Ni@Li$_{2.23}$Mn$_2$O$_4$ showing the morphology of the particles.
Figure 13B:
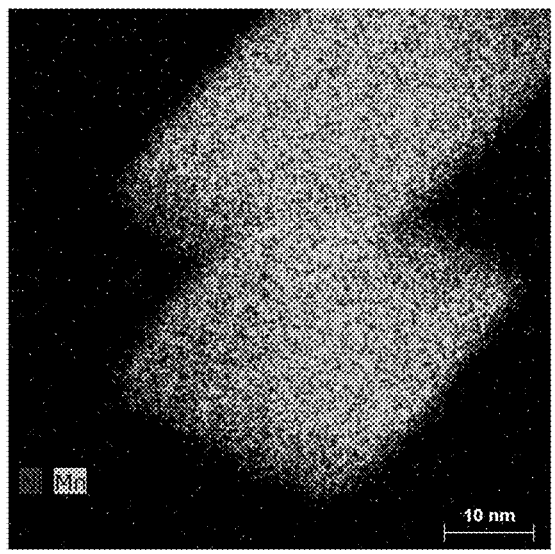
FIG. 13B is mapping of manganese and nickel for Ni@Li$_{2.23}$Mn$_2$O$_4$ using TEM-EDS. The data suggests that Ni is dispersed on the surface of the support and is not agglomerated and that treatment with n-Butyllithium does not change the morphology of the support.

Extension to Lithium Titanate. In order to evaluate the generality of support lithiation as a strategy for modulation of catalyst reactivity, an analogous system was targeted on the reducing anode material lithium titanate. TaNp$_3$Cl$_2$ (Np=Neopentyl) was chemisorbed on anitase TiO$_2$ nanoparticles, which resulted in the release of one equivalent of neopentane per tantalum complex deposited on the surface, suggesting a monopodal binding mode on the surface (or a X$_1$L$_1$ bipodal binding mode with an additional bound lattice oxygen donor), and resulted in Ta/TiO$_2$ with roughly 1.0 wt % Ta on the surface. This material could then be globally reduced with lithium naphthalide, to afford Ta/Li$_x$TiO$_2$ (FIG. 7, top). The reduced and unreduced materials were then exposed to olefin hydrogenation conditions with 0.1 M 1-octene, 1 atmosphere of H$_2$, and 10 mol percent of the Ta catalyst in C$_6$D$_6$ with tritertbutyl benzene as an internal standard. While the parent Ta/TiO$_2$ material was essentially inert under the reaction conditions, the reduced catalyst, Ta/Li$_x$TiO$_2$, proved to be an efficient catalyst, with the appearance of hydrogenated and isomerized products after 2 hours, ~95% conversion after 24 hours, and only trace detectable internal olefins after 144 hours (FIG. 7, bottom).

Definitions

No claim element herein is to be construed under the provisions of 35 U.S.C. § 112(f), unless the element is expressly recited using the phrase "means for."

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic. For example, circuit A communicably "coupled" to circuit B may signify that the circuit A communicates directly with circuit B (i.e., no intermediary) or communicates indirectly with circuit B (e.g., through one or more intermediaries).

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above.

What is claimed is:

1. A method of tuning a catalyst comprising:
   providing a catalyst support precursor having a catalytic metal bound thereto;
   lithiating the catalyst support precursor with the catalytic metal bound thereto; and
   altering the catalyst support precursor with the catalytic metal bound thereto by addition of a charge;
   wherein the catalyst support precursor is selected from the group consisting of a lithium manganese oxide, a lithium titanate, and a nickel manganese cobalt oxide.

2. The method of claim 1, wherein altering the catalyst support precursor comprises intercalation of a metal ion with the catalyst support precursor.

3. The method of claim 1, wherein the catalyst support precursor is a ternary oxide.

4. The method of claim 3, wherein the catalyst support precursor is selected from the group consisting of a lithium manganese oxide, a lithium titanate, and a nickel manganese cobalt oxide.

5. The method of claim 4, wherein the catalytic metal is nickel.

6. The catalyst of claim 4, wherein the catalyst support precursor comprises $Ni_yLi_xMn_2O_4$, where y is 0.40 to 0.6 and wherein x is 0.48 to 1.12.

7. A method of forming a tuned catalyst material comprising:
   providing a catalyst support precursor comprising a ternary oxide; binding a catalytic metal to the catalyst support precursor, the catalytic metal having a sub-monolayer on the catalyst support precursor, forming an untuned catalyst material; and
   altering a charge state of the untuned catalyst material forming a tuned catalyst material.

8. The method of claim 7, wherein altering the catalyst support precursor comprises intercalation of a metal ion with the catalyst support precursor.

9. The method of claim 8, wherein the intercalation is lithiation.

10. The method of claim 9, wherein lithiation includes exposure of an alkyl lithium reagent or an aryl lithium reagent.

11. The method of claim 10, wherein the support is a lithium manganese oxide or lithium titanate.

12. The method of claim 7, wherein the tuned catalyst material has exposed hydroxide groups of the catalyst support precursor.

13. The method of claim 7, wherein the catalyst support precursor is a ternary oxide.

14. The method of claim 7, wherein binding the catalytic metal is by a process selected from the group consisting of: grafting ligand abstraction, condensation, and protonolysis.

* * * * *